(12) United States Patent
Liu et al.

(10) Patent No.: US 7,002,689 B2
(45) Date of Patent: Feb. 21, 2006

(54) OPTICALLY-BASED METHOD AND APPARATUS FOR DETECTING AND CHARACTERIZING SURFACE PITS IN A METAL FILM DURING CHEMICAL MECHANICAL POLISH

(75) Inventors: Hengda Liu, Beaverton, OR (US); Joseph Z. Xie, Shanghai (CN)

(73) Assignee: Rudolph Technologies, Inc., Flanders, NJ (US)

( * ) Notice: Subject to any disclaimer, the term of this patent is extended or adjusted under 35 U.S.C. 154(b) by 412 days.

(21) Appl. No.: 10/105,829

(22) Filed: Mar. 25, 2002

(65) Prior Publication Data

US 2002/0151127 A1    Oct. 17, 2002

Related U.S. Application Data

(60) Provisional application No. 60/283,508, filed on Apr. 12, 2001.

(51) Int. Cl.
*G01N 21/00* (2006.01)
(52) U.S. Cl. .................................................. 356/432
(58) Field of Classification Search ........ 356/432–448, 356/630–632, 32; 73/655, 760, 800, 643; 374/5, 7, 17, 57
See application file for complete search history.

(56) References Cited

U.S. PATENT DOCUMENTS

| | | | |
|---|---|---|---|
| 4,710,030 A | 12/1987 | Tauc et al. | 356/432 |
| 5,674,783 A | 10/1997 | Jang et al. | 437/195 |
| 5,706,094 A | 1/1998 | Maris | 356/432 |
| 5,748,318 A | 5/1998 | Maris et al. | 356/381 |
| 5,780,358 A | 7/1998 | Zhou et al. | 438/645 |
| 5,863,307 A | 1/1999 | Zhou et al. | 51/307 |
| 5,938,504 A | 8/1999 | Talieh | 451/11 |
| 5,976,982 A | 11/1999 | Levy et al. | 438/692 |
| 6,008,906 A | 12/1999 | Maris | 356/432 |
| 6,117,777 A | 9/2000 | Zhou et al. | 438/692 |
| 6,162,728 A | 12/2000 | Tsao et al. | 438/687 |
| 6,179,690 B1 | 1/2001 | Talieh | 451/41 |
| 6,191,855 B1 * | 2/2001 | Maris | 356/244 |
| 6,381,019 B1 * | 4/2002 | Maris | 356/432 |

* cited by examiner

*Primary Examiner*—Tu T. Nguyen
(74) *Attorney, Agent, or Firm*—Harrington & Smith, LLP

(57) ABSTRACT

An optically-based system and method are disclosed for detecting surface pits and their average depth in a metal film by an examination of pulse shape in a reflected probe beam pulse. Also disclosed is an optically-based system and method for detecting an occurrence of a failure in a CMP process by detecting surface pits in a metal film by an examination of pulse shape in a reflected probe beam pulse. Also disclosed is an optically-based system and method for providing quality indications to a CMP process for enabling control of the CMP process by detecting surface pits in a metal film by an examination of pulse shape in a reflected probe beam pulse, where the pulse shape has a twin peak shape that is indicative of a presence of a surface pit.

27 Claims, 5 Drawing Sheets

OPTICALLY-BASED METHOD AND APPARATUS FOR DETECTING AND CHARACTERIZING SURFACE PITS IN A METAL FILM DURING CHEMICAL MECHANICAL POLISH

CLAIM OF PRIORITY FROM COPENDING PROVISIONAL APPLICATION

This patent application claims priority under 37 C.F.R. §1.97(e) from Provisional Patent Application No. 60/283,508, filed Apr. 12, 2001, incorporated by reference herein in its entirety.

FIELD OF THE INVENTION

These teachings relate generally to semiconductor integrated circuit manufacturing processes and, more particularly, relate to a chemical mechanical polish (CMP) process used typically for metal films.

BACKGROUND OF THE INVENTION

CMP is a well known technique for processing films and layers, in particular metal films and layers, during integrated circuit fabrication processes, as evidenced by the following representative U.S. Pat. No. 6,179,690, "Substrate polishing apparatus"; U.S. Pat. No. 6,162,728, "Method to optimize copper chemical-mechanical polishing in copper damascene interconnect process for integrated circuit applications"; U.S. Pat. No. 6,117,777, "Chemical mechanical polish (CMP) endpoint detection by colorimetry"; U.S. Pat. No. 5,976,982, "Methods for protecting device components from chemical mechanical polish induced defects"; U.S. Pat. No. 5,863,307, "Method and slurry composition for chemical-mechanical polish (CMP) planarizing of copper containing conductor layers"; U.S. Pat. No. 5,780,358, "Method for chemical-mechanical polish (CMP) planarizing of copper containing conductor layers"; and U.S. Pat. No. 5,674,783, "Method for improving the chemical-mechanical polish (CMP) uniformity of insulator layers".

It has been observed that surface pitting occurs during the CMP stage of an integrated circuit manufacturing process when using, for example, copper metal films. The presence of these surface pits is undesirable, and is considered a failure mechanism. It is believed that the presence of the pits may cause increased contact resistance and electromigration, as well as Cu residual issues, which can adversely affect device functioning.

At present, the mechanism that causes the pitting is not well understood. The pit failures could originate during the deposition of the copper via an electro-chemical deposition (ECD) process (i.e., plating), or the pit failures could originate during the CMP process itself. If the latter is true then the pitting mechanism may be found to result from overly aggressive chemistry, e.g., the acidic component of the CMP slurry is made too strong. The pits are generally found to have irregular shapes and sizes, typically less than about 30 $\mu m^2$, and a depth of about 10 nm to about 30 nm.

Whatever their cause, the pits are not readily detectable by in-line inspection tools (e.g., optical microscope, AIT2 and CD-SEM). This, obviously, presents a problem to the manufacturers of integrated circuits who employ a CMP process.

SUMMARY OF THE INVENTION

This invention provides a mechanism to detect the occurrence and presence of the pits, preferably a non-contact, optically-based method.

This invention further provides a mechanism to not only detect the occurrence and presence of the pit failures, but to also provide a feedback mechanism for enabling the metal film deposition and/or the polishing process to be controlled so as to avoid the formation of the pit failures.

The foregoing and other problems are overcome by methods and apparatus in accordance with embodiments of this invention.

An optically-based system and method are disclosed for detecting surface pits and their average depth in a metal film by an examination of pulse shape in a reflected beam of light, typically embodied as a reflected probe beam pulse.

Also disclosed is an optically-based system and method for detecting an occurrence of a failure in a CMP process by detecting surface pits in a metal film by an examination of pulse shape in a reflected probe beam pulse.

Also disclosed is an optically-based system and method for providing quality indications to a CMP process for enabling control of the CMP process by detecting surface pits in a metal film by an examination of pulse shape in a reflected probe beam pulse, where the pulse shape has a twin peak shape that is indicative of a presence of a surface pit. Control of the CMP process may include controlling at least one of polish pressure, speed, polish pad life and polish slurry composition and chemistry.

Also disclosed is an optically-based system and method to enable semiconductor process improvements using an optical metrology system that is suitably programmed to recognize and detect the presence of an abnormal (twin) peak that is indicative of a surface defect (e.g., pitting) in a film (e.g., a metal (Cu) film).

BRIEF DESCRIPTION OF THE DRAWINGS

The above set forth and other features are made more apparent in the ensuing Detailed Description of the Preferred Embodiments when read in conjunction with the attached Drawings, wherein.

DETAILED DESCRIPTION OF THE PREFERRED EMBODIMENTS

Figure 1:
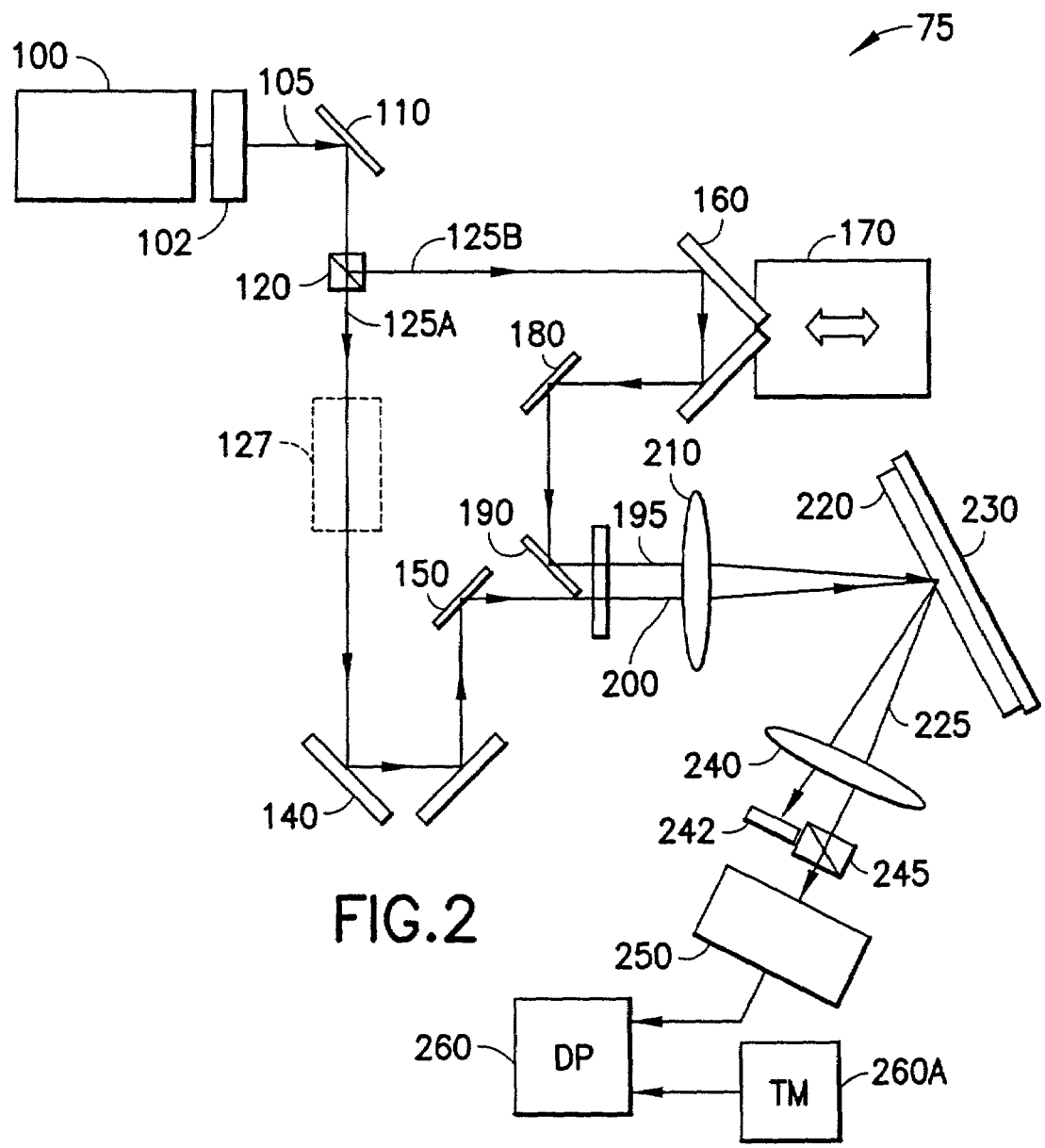
FIG. 1 is a block diagram of an optical metrology system that is suitable for practicing this invention.
Figure 1:
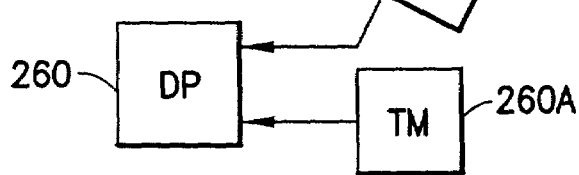

FIG. 1 is a schematic depiction of a non-limiting embodiment of a photoacoustic film thickness measurement system 75, with optical paths shown, that is suitable for use in practicing these teachings. General reference in this regard may be had to the following representative U.S. Pat. Nos. 4,710,030, "Optical generator of stress pulse"; U.S. Pat. No. 5,706,094, "Ultrafast optical technique for the characterization of altered materials"; U.S. Pat. No. 5,748,318, "Optical stress generator and detector"; and U.S. Pat. No. 6,008,906, "Optical method for the characterization of the electrical properties of semiconductors and insulating films", the disclosures of which are incorporated by reference herein in their entireties.

The photoacoustic measurement system 75 includes a pulsed light source 100, a sample stage 220, a vacuum chuck 230, a first probe beam steering mirror 180, a pump beam steering mirror 150, a first steering mirror 110, and a pump-probe beamsplitter 120. Additionally, the photoacoustic system 75 includes a probe retroreflector 160, a delay scanning stage 170, a beam dump 242, and a detector 250. Furthermore, photoacoustic measurement system 75 includes a linear pump-discriminating polarizer 245, a harmonic generator wavelength selector (wavelength selector) 102, a projecting lens 210, a collimating lens 240, a pump retroreflector 140, a EOM-polarizer assembly 127, and a second probe beam steering mirror 190.

The pulsed light source 100 may be a titanium-sapphire laser operating at 80 MHz and emitting light at 800 nm. The laser can also be alternatively configured with a frequency doubling birefringent crystal to emit laser beam 105 at 400 nm. The light source 100 could as well be an x-ray source, a synchrotron source, or an excimer laser source.

In operation, pulsed light source 100 emits laser beam 105 that may be re-directed by first steering mirror 110. Pump/probe beamsplitter 120 splits the incident laser beam pulse (preferably of picosecond or shorter duration) into pump beam 125A and probe beam 125B.

EOM-polarizer assembly 127 rotates pump beam 125A at a frequency of several MHz and converts polarized and rotated pump beam 125A into amplitude modulated pump beam 200. Pump retroreflector 140 and pump beam steering mirror 150 deflect modulated pump beam 200 onto sample stage 220.

Probe beam 125B is transmitted to probe retroreflector 160 where delay scanning stage 170 is used to modify probe beam 125B profile at the output of retroreflector 160, forming time delayed probe beam 195.

Delayed probe beam 195 and modulated pump beam 200 propagate through projecting lens 210. Sample stage 220 is held in place by vacuum chuck 230 and acts as a positioning unit for a wafer (not shown), and is preferably a multiple-degree of freedom stage that is adjustable in height (z-axis), position (x and y-axes), and tilt (θ), and allows motor controlled positioning of a portion of the sample relative to the modulated pump beam 200 and delayed probe beam 195. The z-axis is used to translate the sample vertically into the focus region of the pump and probe beams, the x and y-axes translate the sample parallel to the focal plane, and the tilt axes adjust the orientation of the stage sample 220 to establish a desired angle of incidence for the probe beam 195.

Modulated pump beam 200 and delayed probe beam 195 propagate through collimating lens 240 where the modulated pump beam 200 is gathered by beam dump 242. The pump-discriminating polarizer 245 isolates the reflected probe beam 225 from modulated pump beam 200, and detector 250 converts reflected probe beam 225 into a correction signal that is applied to dither AOM 205. The output of the detector 250 is also provided as an input to a data processor (DP) 260 that is programmed to characterize a sample that is placed on the sample stage 220.

In accordance with the teachings herein, the data processor 260 is also used to detect the presence of surface pits in a metal film, such as surface pits that occur during a CMP process on a Cu film as was described above, in addition to the measurement of film thickness by the time delay between the application of the pump pulse and the resulting "echo" observed in the reflected probe beam.

Figure 2A:
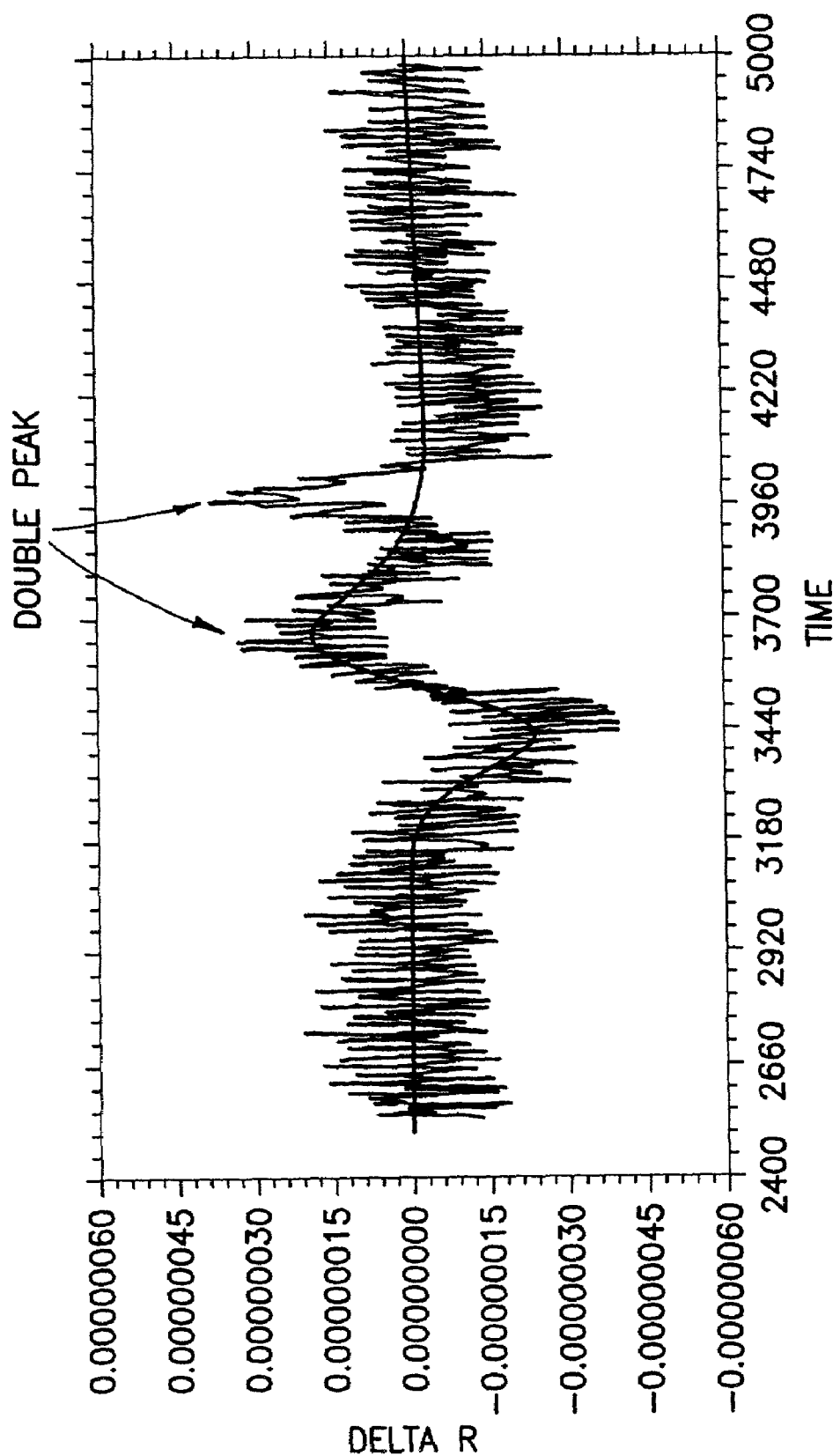
FIGS. 2A and 2B are each an example of a twin peak in a reflected probe pulse that has been found to be indicative of the presence of a pit in a Cu film surface.
Figure 2B:
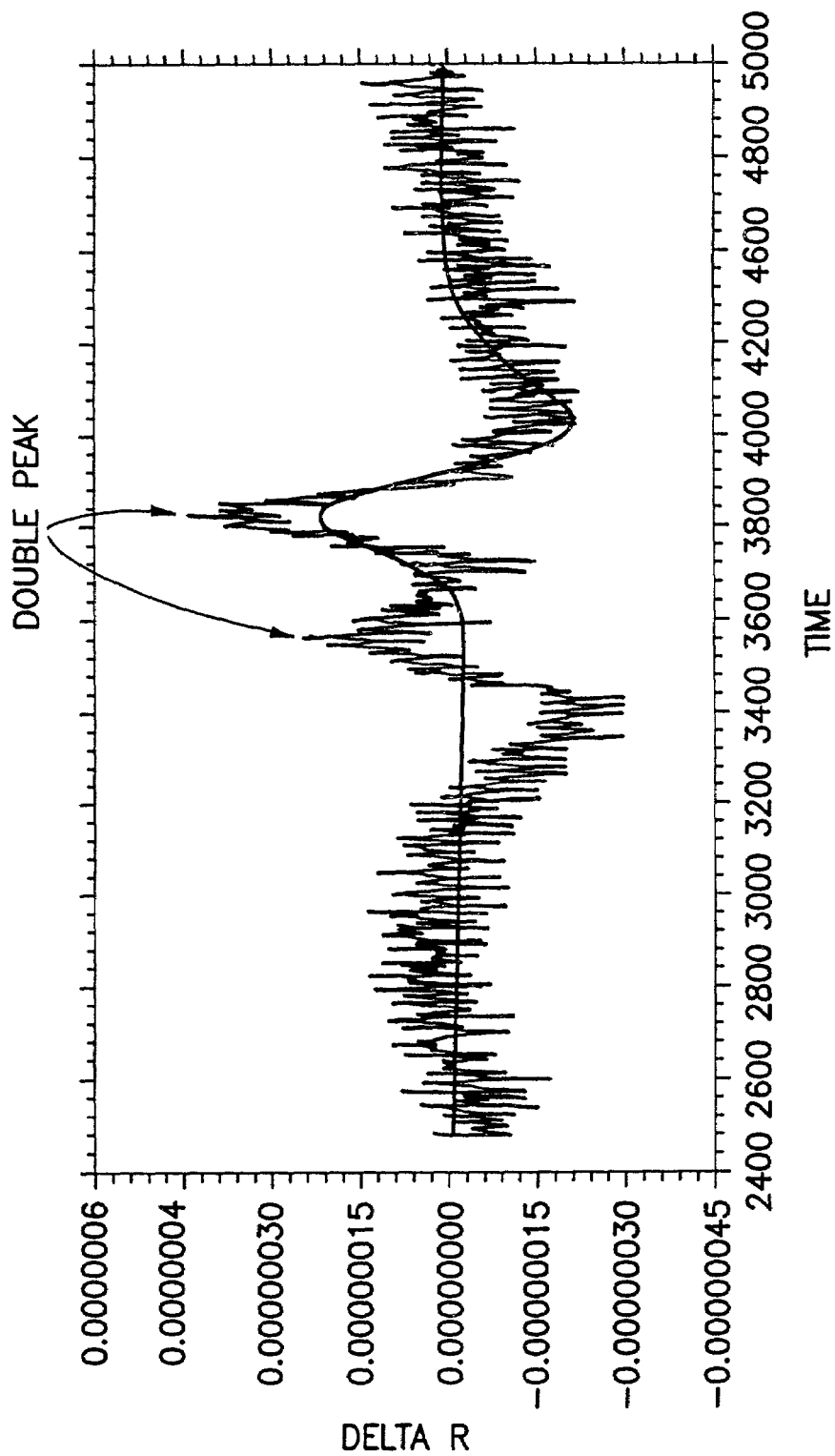
Figure 2C:
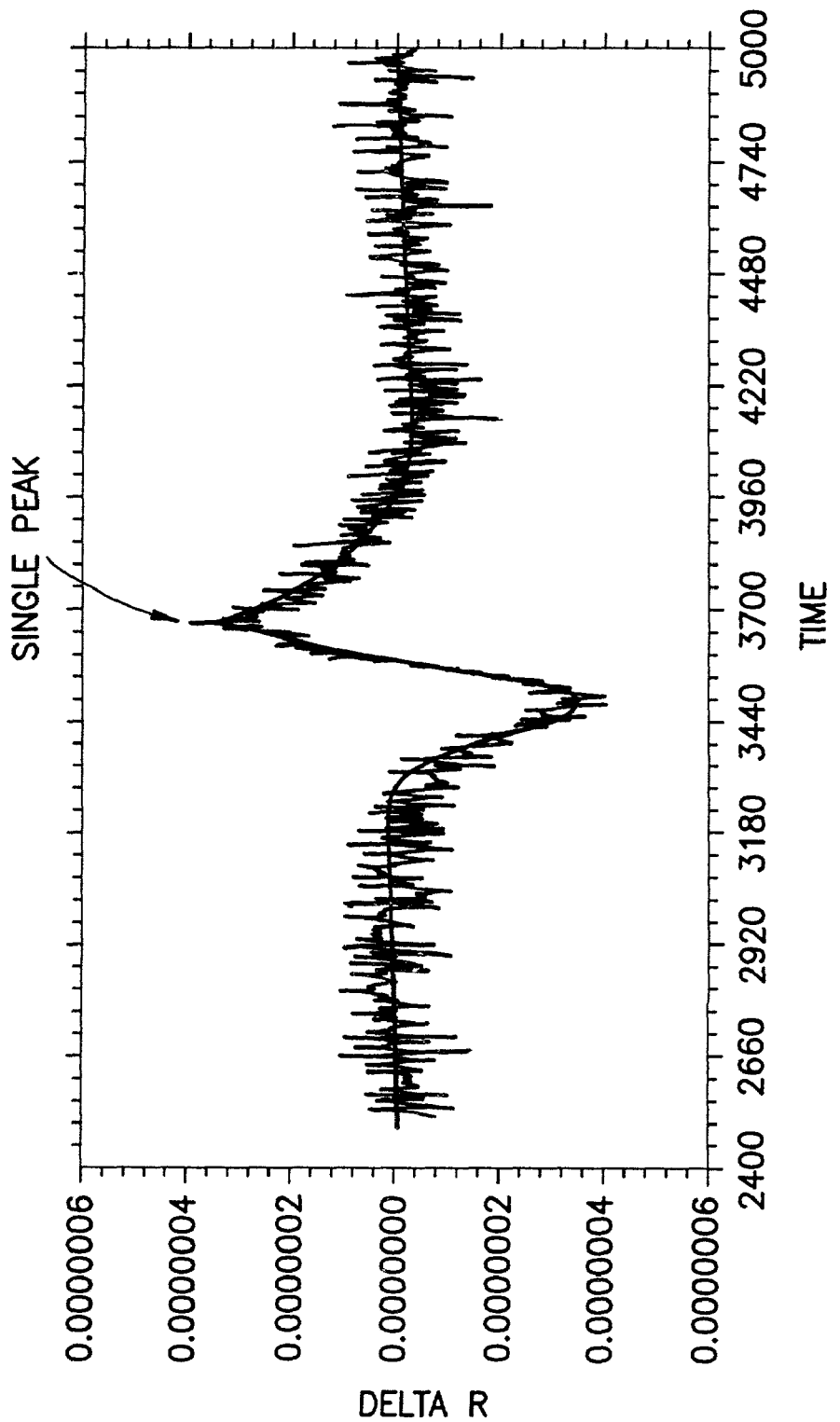
FIG. 2C is an example of a normal (non-twinned) peak obtained from a smooth (nonpitted) portion of the Cu film surface.

It has been observed that the presence of a pit is indicated by the presence of a "double peak", also referred to herein as a "twin peak", in the detected probe pulse, two examples of which are shown in FIGS. 2A and 2B. On a smooth (non-pitted) portion of the Cu film a normal, single peak (FIG. 2C) is observed in the reflected probe pulse energy. The presence of a twin peak in the reflected probe pulse is thus deemed to be indicative of the presence of a pit in the Cu film surface.

Figure 3:
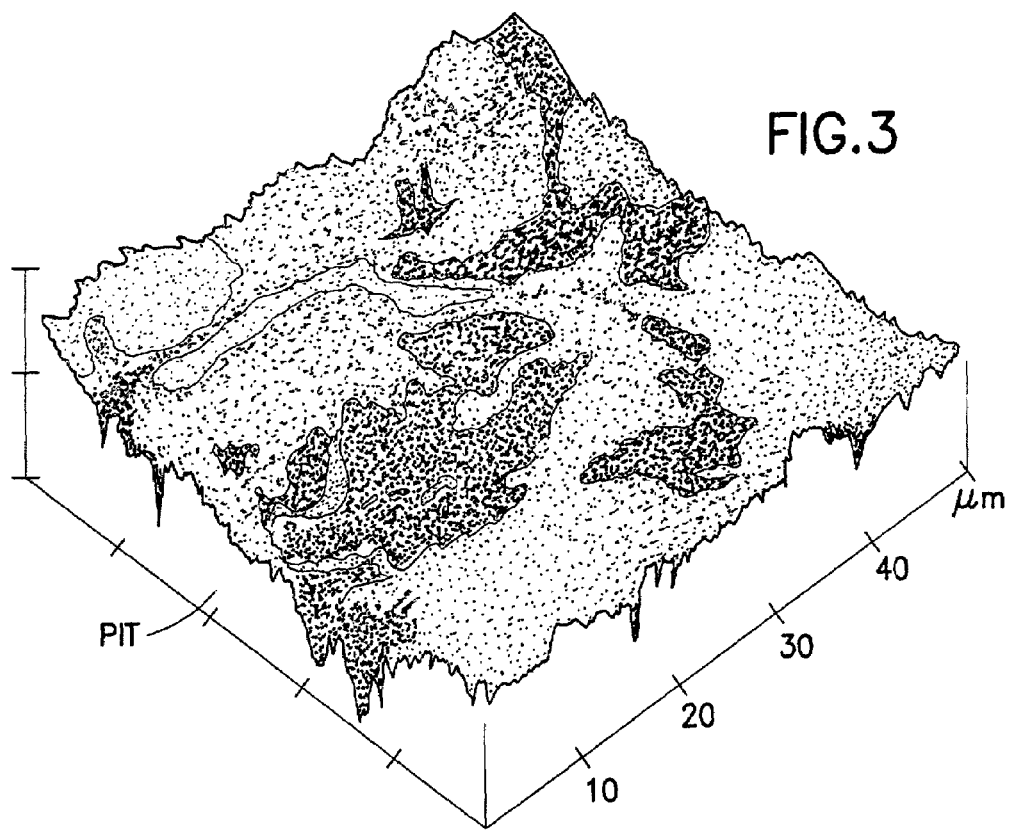
FIG. 3 is an Atomic Force Microscope (AFM) image of a pit that was located in a Cu film after a CMP process, where the location of the pit was indicated by the presence of a twin peak in the reflected probe pulse.

FIG. 3 is an Atomic Force Microscope (AFM) image of a pit that was located in a Cu film after a CMP process, where the location of the pit was indicated by the presence of a twin peak in the reflected probe pulse.

It has been found that the depth of the pits is typically less than the separation between the peaks of the twin peak pair, enabling an indication of pit depth to be ascertained.

It can thus be appreciated that the optical metrology system 75 of FIG. 1 can be used to conduct defect metrology, whereby a metal film deposition or polishing process can be monitored, and possibly controlled as well.

Figure 4:
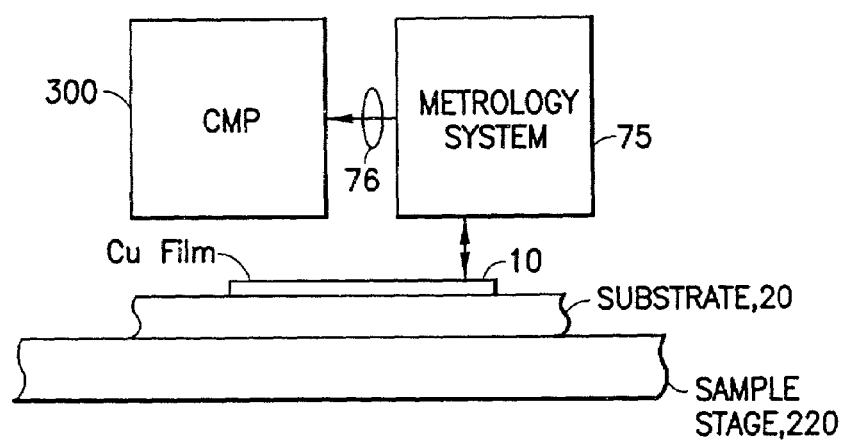
FIG. 4 is a block diagram showing the optical metrology system of FIG. 1 being used to provide quality-related feedback to a CMP process so as to eliminate or minimize a number of pits formed in a metal film.

FIG. 4 is a block diagram showing the optical metrology system 75 of FIG. 1 being used to provide film thickness as well as quality-related feedback 76 to a CMP process 300 so as to eliminate or minimize a number of pits formed in a metal (e.g., Cu) film 10. The Cu film 10 is assumed to be disposed upon or over a substrate 20, such as an integrated circuit, that may in turn be disposed on the sample stage 220 of FIG. 1. In this approach the output of the DP 260 is monitored for the occurrence of twin peaks in the probe beam reflectivity data, and the CMP process 300 is controlled or varied in a closed loop fashion to drive the error (i.e., the presence of pits in the Cu film 10) towards zero. CMP parameters that may be controlled by the quality indication feedback 76 include polish pressure, speed, polish pad life and polish slurry composition and chemistry. Note that the feedback need not be direct, but could be through some intermediary, including a human operator.

In a related fashion the optical metrology system 75 can also be used to monitor other characteristics of the metal film 10, such as sudden increases in thickness, and the resulting feedback is employed to control the process that forms or that operates on the metal film.

These teachings thus provide a technique for detecting surface pits and their average depth, as well as a technique for detecting an occurrence of a failure in a CMP process by the detection of surface pits, as well as a technique to provide quality measurements to a CMP process for enabling control of the CMP process.

Semiconductor process improvements (e.g., yield improvements) are thus made possible by the use of the optical metrology system 75, when suitably programmed to recognize and detect the presence of abnormal (twin) peaks indicative of a surface defect (e.g., pitting) in a film (e.g., a metal (Cu) film). For example, the DP 260 can operate in accordance with a stored program to algorithmically process the pulse shape of the reflected probe pulse to detect the characteristic double peak shape, or it could compare the pulse shape to a template of pulse shapes stored in a template memory (TM) 260A, at least some of which are indicative of the occurrence of a surface pit. Various double peak pulse shape templates can be obtained from known examples of surface pits having different depths and shapes, such as those shown in FIGS. 2A and 2B, so as to facilitate the recognition of unknown surface pits.

While these teachings have been particularly shown and described with respect to preferred embodiments thereof, it will be understood by those skilled in the art that changes in form and details may be made therein without departing from the scope and spirit of the invention. For example, these teachings are limited to characterizing only copper-containing films, or only metal films.

What is claimed is:

1. An optically-based metrology system comprising means for generating pump and probe pulse pairs that are directed to a surface of a film layer disposed over a substrate, a detector for detecting reflected probe pulses, and a processor having an input coupled to an output of said detector for detecting a presence of a surface pit in the film layer by an examination of the pulse shape of the reflected probe pulses.

2. An optically-based metrology system comprising means for generating pump and probe pulse pairs that are directed to a surface of a film layer disposed over a substrate, a detector for detecting reflected probe pulses, and a processor having an input coupled to an output of said detector for detecting a presence of a surface pit in the film layer by an examination of the pulse shape of the reflected probe pulses, where the resulting pulse shape is characterized by a double peak.

3. An optically-based metrology system having an output for indicating an occurrence of a failure in a chemical mechanical polish process performed on a metal film, comprising means for generating pump and probe pulse pairs that are directed to a surface of the metal film, a detector for detecting reflected probe pulses, and a processor having an input coupled to an output of said detector for detecting a presence of a surface pit in the metal film by an examination of the pulse shape of the reflected probe pulses, where the pulse shape is characterized by a double peak.

4. An optically-based metrology system for providing a quality indication to a chemical mechanical polish (CMP) process, said system having an output coupled to the CMP process for indicating an occurrence of a defect in a metal film, comprising means for generating pump and probe pulse pairs that are directed to a surface of the metal film, a detector for detecting reflected probe pulses, and a processor having an input coupled to an output of said detector for detecting a presence of a surface pit in the metal film by an examination of the pulse shape of the reflected probe pulses, where the pulse shape is characterized by a double peak and is indicative of a metal film defect.

5. An optically-based metrology system as in claim 4, and further employing the optical metrology system to measure a thickness of the metal film.

6. An optically-based metrology system as in claim 4, where the metal film is comprised of copper.

7. An optically-based metrology system as in claim 4, where the CMP process is responsive to the system output indicating the occurrence of the defect for controlling at least one of polish pressure, speed, polish pad life and polish slurry composition and chemistry.

8. A method for operating a metrology system, comprising: generating pump and probe pulse pairs that are directed to a surface of a metal film, detecting reflected probe pulses, and examining the pulse shape of the reflected probe pulses for detecting a presence of a surface pit in the metal film.

9. A method as in claim 8, further comprising determining an indication of pit depth from the pulse shape.

10. A method for operating a metrology system, comprising: generating pump and probe pulse pairs that are directed to a surface of a metal film, detecting reflected probe pulses, and examining the pulse shape of the reflected probe pulses for detecting a presence of a surface pit in the metal film, where the pulse shape is characterized by a double peak.

11. A method for indicating an occurrence of a failure in a chemical mechanical polish process performed on a metal film, comprising: generating pump and probe pulse pairs that are directed to a surface of the metal film, detecting reflected probe pulses, and examining the pulse shape of the reflected probe pulses for detecting a presence of a surface pit in the metal film, where the pulse shape is characterized by a double peak.

12. A method for providing a quality indication to a chemical mechanical polish (CMP) process, the quality indication comprising an occurrence of a defect in a metal film, comprising: generating pump and probe pulse pairs that are directed to a surface of the metal film, detecting reflected probe pulses, and detecting a presence of a surface pit in the metal film by an examination of the pulse shape of the reflected probe pulses, where the pulse shape is characterized by a double peak and is indicative of a metal film defect.

13. A method as in claim 12, where the CMP process is responsive to the indication of the occurrence of the defect for controlling at least one of polish pressure, speed, polish pad life and polish slurry composition and chemistry.

14. A method as in claim 12, and further comprising measuring a thickness of the metal film.

15. A method as in claim 12, where the metal film is comprised of copper.

16. A metrology system comprising at least one light source to generate pump pulses and probe pulses directed towards a surface of a sample, a light detector positioned to convert probe pulses that impinge on the surface of the sample to electrical signal pulses at an output of said light detector, and a data processor having an input coupled to said output of said light detector, said data processor operating in accordance with a stored program to detect a presence of a pit in the surface of the sample through an examination of the shape of the electrical signal pulses.

17. A metrology system as in claim 16, where said data processor operates further in accordance with the stored program to indicate an outcome of a polishing process performed on the surface.

18. A metrology system as in claim 16, where said data processor operates further in accordance with the stored program to provide quality-related feedback information to a polishing process that is performed on the surface.

19. A metrology system as in claim 16, where said data processor operates further in accordance with the stored program in a feedback loop of a polishing process that is performed on the surface.

20. A metrology system as in claim 16, where the sample is comprised of a semiconductor substrate having a metal layer disposed on a surface thereof, where the probe pulses impinge on a surface of the metal layer, and where data processor operates further in accordance with the stored program to provide quality-related feedback information to a process that operates on the metal layer.

21. A metrology system as in claim 16, where said data processor operates in accordance with the stored program to detect the presence of a pit in the surface of the sample through an algorithmic examination of the shape of the electrical signal pulses.

22. A metrology system as in claim 16, where said data processor operates in accordance with the stored program to detect the presence of a pit in the surface of the sample through a comparison of the shape of the electrical signal pulses to a set of pulse shape templates stored in a memory that is readably coupled to the data processor.

23. A metrology system as in claim 16 wherein said program is stored on a memory device.

24. A metrology system comprising at least one light source to generate pump pulses and probe pulses directed towards a surface of a sample, a light detector positioned to convert probe pulses that impinge on the surface of the sample to electrical signal pulses at an output of said light detector, and a data processor having an input coupled to said output of said light detector, said data processor operating in accordance with a stored program to detect a presence of a pit in the surface of the sample through an examination of the shape of the electrical signal pulses, where the data processor detects the presence of the pit in the surface when the examination finds two peaks in the shape of the electrical signal pulses.

25. A metrology system as in claim 24, where the data processor further ascertains an indication of the depth of the pit from a spacing between the two peaks.

26. A memory, said memory for being readably coupled to a data processor that forms a part of a metrology system that generates electrical signal pulses from light pulses that impinge on a surface of a sample, said data processor operating in accordance with a stored program to detect a presence of a pit in the surface of the sample through an examination of the shape of the electrical signal pulses, said memory storing a set of pulse shape templates that said data processor compares to the shape of the electrical signal pulses, said data processor operating in accordance with the stored program to detect a presence of a pit in the surface when the shape of the electrical signal pulses matches a pulse shape template characterized as having two peaks.

27. A memory as in claim 26, where the sample is comprised of a semiconductor substrate having a metal layer disposed on a surface thereof, and where the light pulses comprise probe beam pulses that impinge on a surface of the metal layer.

* * * * *